(12) United States Patent
Mingozzi et al.

(10) Patent No.: US 9,155,560 B2
(45) Date of Patent: Oct. 13, 2015

(54) MULTI-PURPOSE EXTERNAL FIXATOR

(75) Inventors: Franco Mingozzi, Calderara di Reno (IT); Alan Dovesi, Bologna (IT)

(73) Assignee: CITIEFFE S.R.L. (IT)

( * ) Notice: Subject to any disclaimer, the term of this patent is extended or adjusted under 35 U.S.C. 154(b) by 121 days.

(21) Appl. No.: 13/501,655

(22) PCT Filed: Oct. 15, 2010

(86) PCT No.: PCT/IB2010/054681
§ 371 (c)(1),
(2), (4) Date: Apr. 12, 2012

(87) PCT Pub. No.: WO2011/055252
PCT Pub. Date: May 12, 2011

(65) Prior Publication Data
US 2012/0203225 A1    Aug. 9, 2012

(30) Foreign Application Priority Data

Nov. 5, 2009   (IT) .............................. BO2009A0726

(51) Int. Cl.
  *A61B 17/00*  (2006.01)
  *A61F 4/00*   (2006.01)
  *A61F 5/04*   (2006.01)
  *A61B 17/64*  (2006.01)

(52) U.S. Cl.
  CPC ......... *A61B 17/6466* (2013.01); *A61B 17/6416* (2013.01)

(58) Field of Classification Search
  CPC ........................................... A61B 17/60–17/68
  USPC .............. 606/53–60, 246, 250–253, 264–278
  See application file for complete search history.

(56) References Cited

U.S. PATENT DOCUMENTS

| 1,706,215 A | * | 3/1929 | Davidson ........................ 403/97 |
| 4,700,437 A | * | 10/1987 | Hoshino ........................ 24/456 |
| 5,427,465 A | * | 6/1995 | Sato ............................... 403/49 |
| 5,727,899 A | * | 3/1998 | Dobrovolny .................. 403/389 |

(Continued)

FOREIGN PATENT DOCUMENTS

| DE | 20016839 | 12/2000 |
| EP | 0972491 | 1/2000 |

OTHER PUBLICATIONS

International Search Report dated Dec. 3, 2010 and Written Opinion from related application.

*Primary Examiner* — Eduardo C Robert
*Assistant Examiner* — Michelle C Eckman
(74) *Attorney, Agent, or Firm* — Timothy J. Klima; Shuttleworth & Ingersoll, PLC

(57) ABSTRACT

A multi-purpose external fixator (1) comprises at least one screw (2) to be implanted in a bone fragment (3) and a frame (7), in turn comprising at least one clamp (8) and at least one bar (9); the clamp (8) comprising a central body (11), in which a slot (12) is made for connection to the screw (2), an element (13) for locking the screw (2) in the slot (12) and a lever (14) for operating the locking element (13); the lever (14) is hinged to the central body (11) and can move away from and towards an end position for engagement of the locking element (13) and stable connection of the screw (2) to the slot (12); in the end position the lever (14) and the screw (2) are positioned in a T-shaped configuration relative to each other, in which the lever (14) forms a grip for implanting the screw (2) in the bone fragment.

19 Claims, 5 Drawing Sheets

(56) References Cited

U.S. PATENT DOCUMENTS

| | | | |
|---|---|---|---|
| 5,976,133 A * | 11/1999 | Kraus et al. | 606/54 |
| 6,080,153 A * | 6/2000 | Mata et al. | 606/54 |
| 6,264,396 B1 * | 7/2001 | Dobrovolny | 403/391 |
| 6,277,069 B1 * | 8/2001 | Gray | 600/234 |
| 6,309,389 B1 * | 10/2001 | Baccelli | 606/264 |
| 6,652,523 B1 * | 11/2003 | Evrard et al. | 606/54 |
| 6,736,775 B2 * | 5/2004 | Phillips | 600/234 |
| 7,166,108 B2 * | 1/2007 | Mazda et al. | 606/305 |
| 7,241,074 B2 * | 7/2007 | Thomke et al. | 403/385 |
| 7,314,331 B1 * | 1/2008 | Koros et al. | 403/396 |
| 7,562,855 B2 * | 7/2009 | Oetlinger | 248/316.6 |
| 7,594,924 B2 * | 9/2009 | Albert et al. | 606/267 |
| 7,708,736 B2 * | 5/2010 | Mullaney | 606/54 |
| 7,938,829 B2 * | 5/2011 | Mullaney | 606/59 |
| 8,241,285 B2 * | 8/2012 | Mullaney | 606/59 |
| 8,246,561 B1 * | 8/2012 | Agee et al. | 602/22 |
| 2001/0004432 A1 * | 6/2001 | Pfister | 403/188 |
| 2002/0061225 A1 * | 5/2002 | Boucher et al. | 403/386 |
| 2002/0151892 A1 * | 10/2002 | Walulik et al. | 606/57 |
| 2003/0004511 A1 * | 1/2003 | Ferree | 606/61 |
| 2003/0153910 A1 | 8/2003 | Janowski et al. | |
| 2004/0039385 A1 * | 2/2004 | Mazda et al. | 606/61 |
| 2004/0116929 A1 * | 6/2004 | Barker et al. | 606/61 |
| 2005/0085810 A1 * | 4/2005 | Lutz et al. | 606/54 |
| 2005/0131404 A1 * | 6/2005 | Mazda et al. | 606/61 |
| 2006/0229616 A1 * | 10/2006 | Albert et al. | 606/61 |
| 2007/0038217 A1 * | 2/2007 | Brown et al. | 606/57 |
| 2007/0049932 A1 * | 3/2007 | Richelsoph et al. | 606/61 |
| 2007/0198012 A1 * | 8/2007 | Thomke et al. | 606/54 |
| 2008/0234756 A1 * | 9/2008 | Sutcliffe et al. | 606/308 |
| 2009/0036891 A1 * | 2/2009 | Brown et al. | 606/57 |
| 2009/0088751 A1 * | 4/2009 | Mullaney | 606/59 |
| 2009/0148232 A1 * | 6/2009 | Thomke et al. | 403/373 |
| 2009/0306661 A1 * | 12/2009 | Thomke et al. | 606/54 |
| 2010/0234844 A1 * | 9/2010 | Edelhauser et al. | 606/56 |
| 2010/0234845 A1 * | 9/2010 | Mullaney | 606/56 |
| 2010/0298827 A1 * | 11/2010 | Cremer et al. | 606/54 |
| 2011/0034960 A1 * | 2/2011 | Schmucki et al. | 606/324 |
| 2011/0077689 A1 * | 3/2011 | Mickiewicz et al. | 606/277 |
| 2011/0087226 A1 * | 4/2011 | Murner et al. | 606/54 |
| 2011/0098706 A1 * | 4/2011 | Mullaney | 606/54 |
| 2011/0098707 A1 * | 4/2011 | Mullaney | 606/59 |
| 2011/0112533 A1 * | 5/2011 | Venturini et al. | 606/54 |
| 2011/0172663 A1 * | 7/2011 | Mullaney | 606/59 |
| 2011/0196425 A1 * | 8/2011 | Rezach et al. | 606/278 |
| 2011/0264094 A1 * | 10/2011 | Cunliffe et al. | 606/59 |
| 2012/0004659 A1 * | 1/2012 | Miller et al. | 606/54 |
| 2012/0095462 A1 * | 4/2012 | Miller | 606/59 |
| 2012/0150180 A1 * | 6/2012 | Verma et al. | 606/59 |
| 2012/0150181 A1 * | 6/2012 | Dorawa et al. | 606/59 |
| 2012/0150182 A1 * | 6/2012 | Dominik et al. | 606/59 |
| 2012/0150183 A1 * | 6/2012 | Dorawa et al. | 606/59 |
| 2012/0150184 A1 * | 6/2012 | Mullaney | 606/59 |
| 2012/0150185 A1 * | 6/2012 | Mullaney | 606/59 |
| 2012/0197297 A1 * | 8/2012 | Bootwala et al. | 606/246 |
| 2012/0209266 A1 * | 8/2012 | Ottoboni et al. | 606/59 |
| 2012/0259369 A1 * | 10/2012 | Hammer | 606/251 |
| 2012/0289959 A1 * | 11/2012 | Miller | 606/59 |
| 2012/0296335 A1 * | 11/2012 | Mullaney | 606/59 |

* cited by examiner

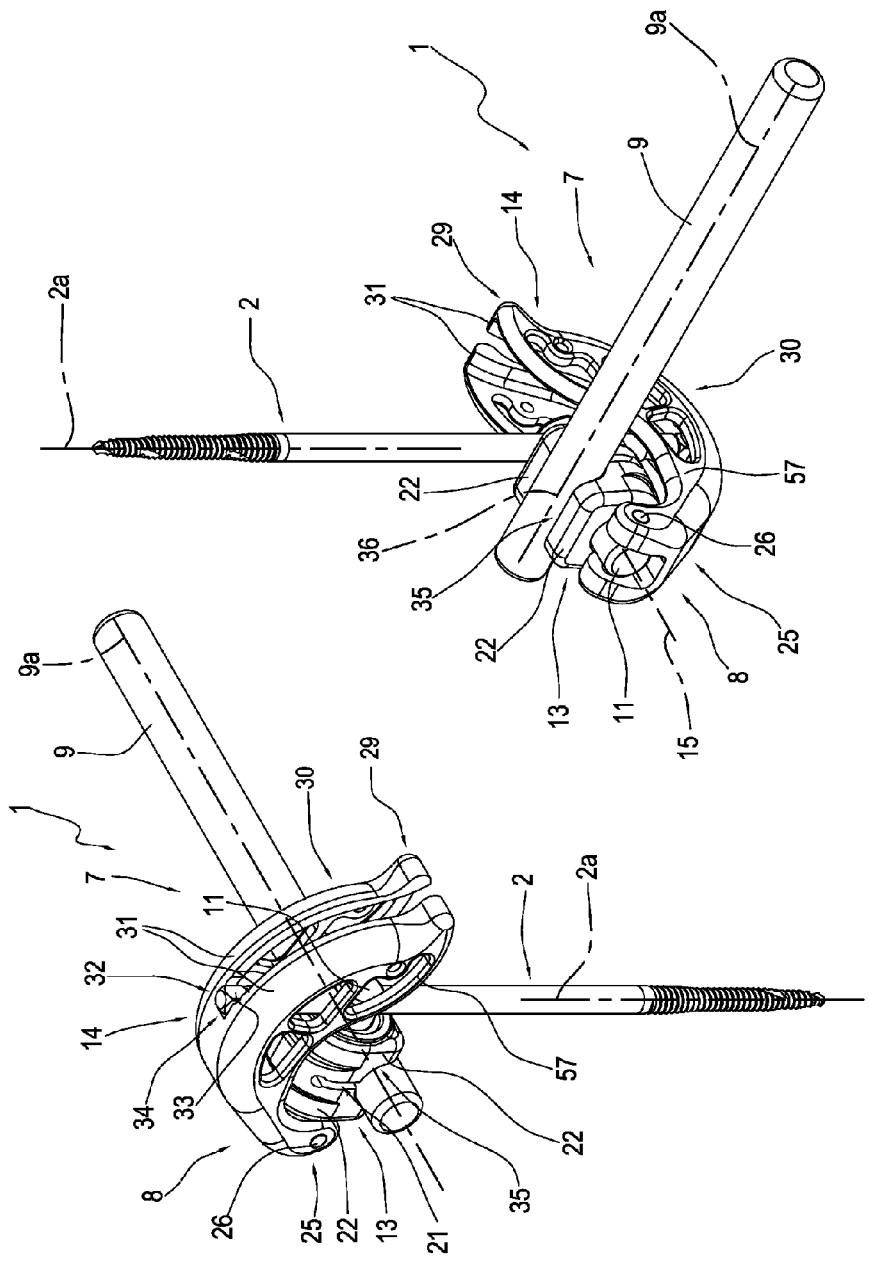

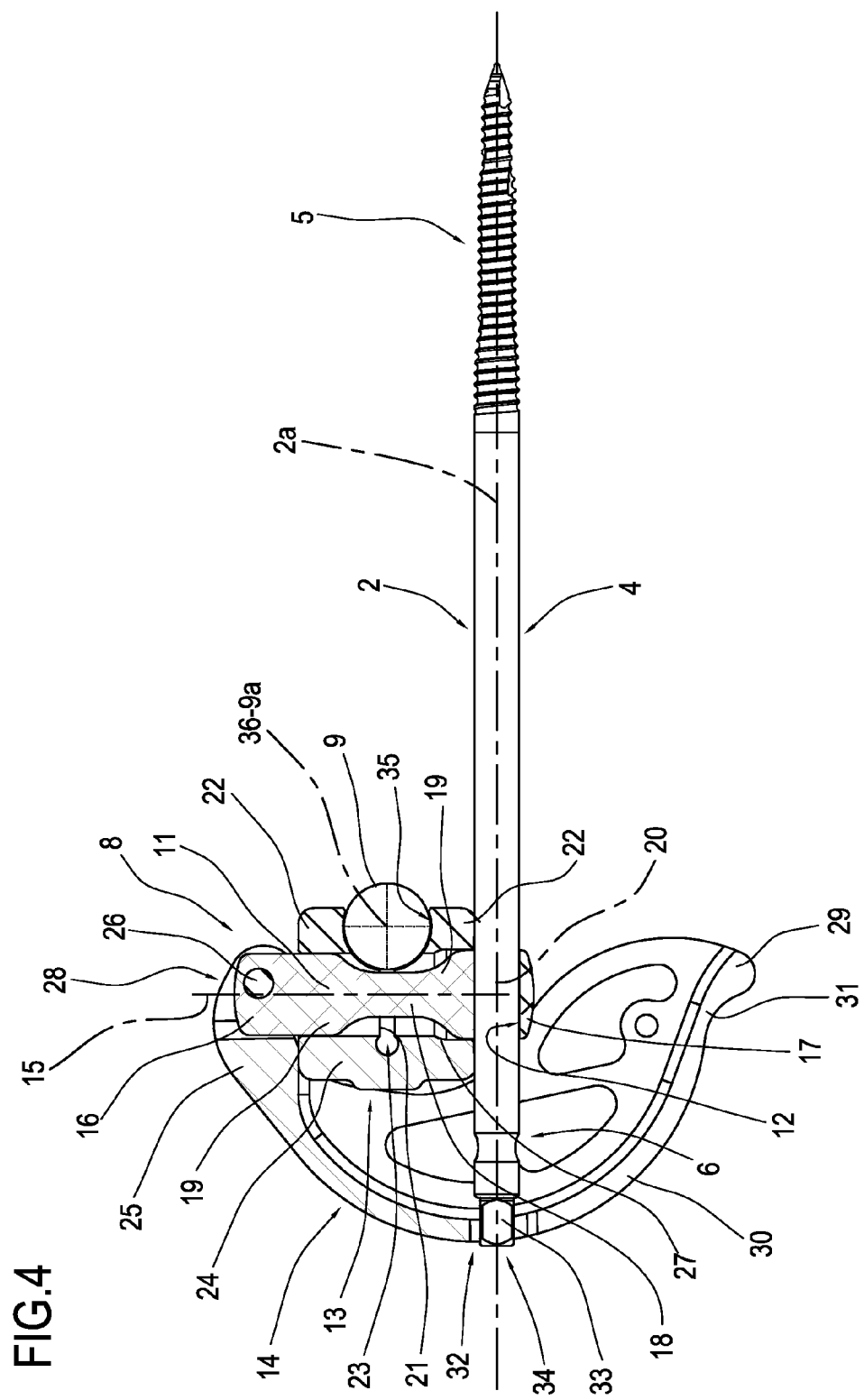

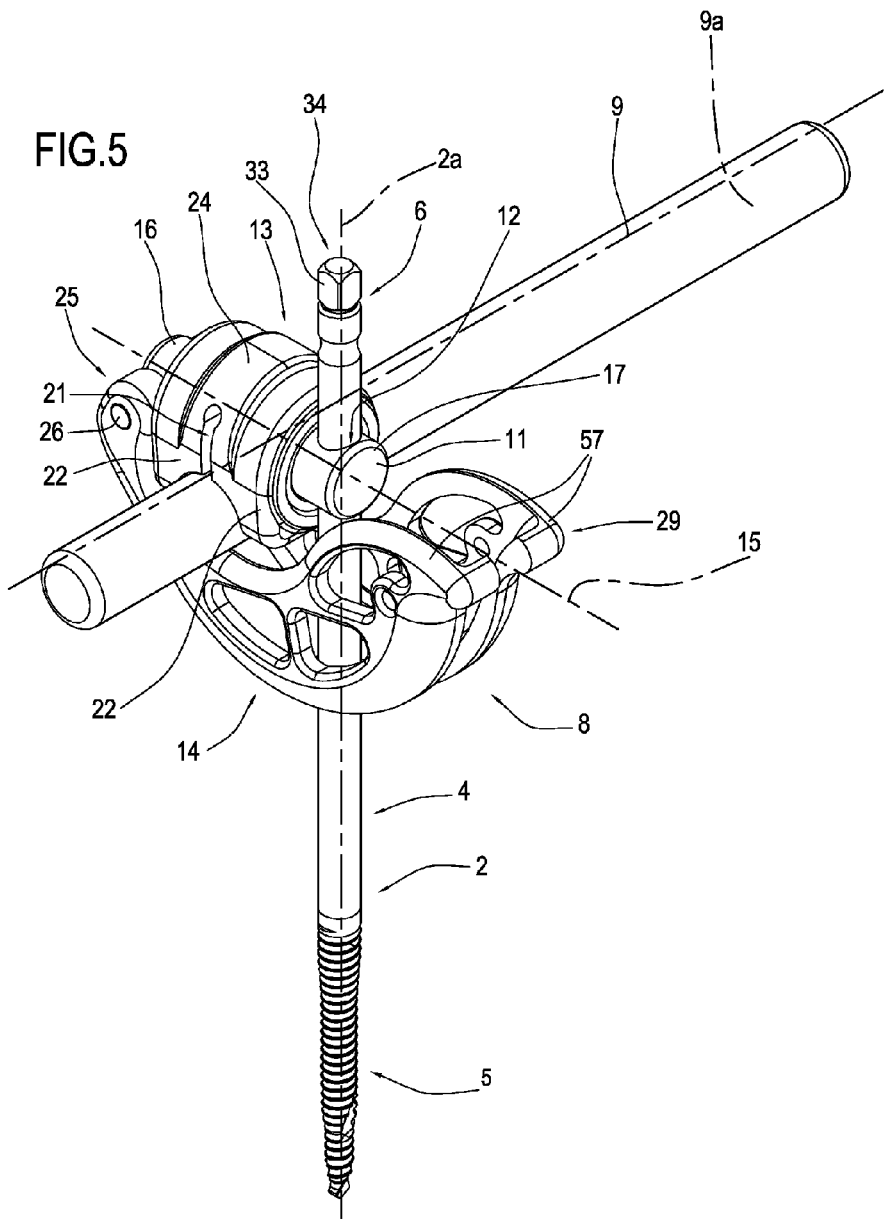

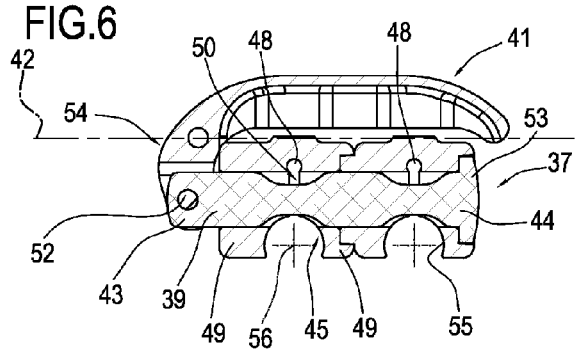
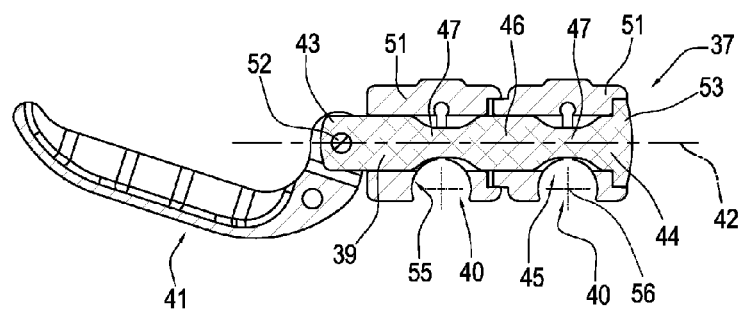
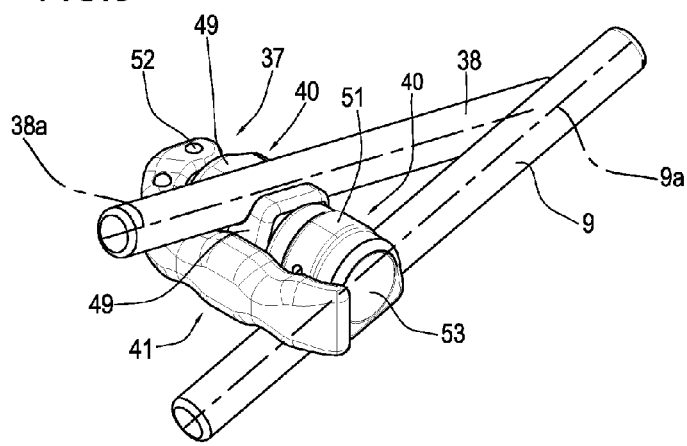

MULTI-PURPOSE EXTERNAL FIXATOR

This application is the National Phase of International Application PCT/IB2010/054681 filed Oct. 15, 2010 which designated the U.S. and that International Application was published under PCT Article 21(2) in English.

This application claims priority to Italian Patent Application No. BO2009A000726 filed Nov. 5, 2009 and PCT Application No. PCT/IB2010/054681 filed Oct. 15, 2010, which applications are incorporated by reference herein.

TECHNICAL FIELD

This invention relates to a multi-purpose external fixator.

BACKGROUND ART

In orthopaedics, for several years a technique has been known for stabilising fractures without using external fixators instead of conventional plaster casts.

External fixators usually comprise a plurality of bone screws, normally in pairs, which are implanted in the bone fragments of the fracture in such a way that the head ends of the screws project from the skin of the patient. Said ends are anchored to a rigid external frame which is equipped with clamps and joints which can be orientated in such a way as to allow them to be adjusted to the position of the screws.

The screws usually have a cylindrical body, delimited on one side by a threaded end designed to be screwed into the bone fragment, and on the other side by the above-mentioned head end, which is shaped in such a way that it can be connected to a temporary grip which allows the screw to be screwed into the bone fragment. The connection between the screw and the grip is normally of the male-female type with quick coupling and release.

When operating, after making an incision in the soft tissue, the surgeon makes holes in the bone fragments on opposite sides of the fracture fissure and implants the screws in the holes. Then the surgeon connects the screw, without the temporary grip attached, to the respective clamps of the frame. If necessary, the surgeon then performs an operation called "reduction", that is to say, with the aid of radiological equipment (luminance amplifier) he aligns the edges of the fracture in such a way as to arrange the bone fragments in the most suitable position to knit together.

Once the fracture has been reduced, the surgeon locks the joints and clamps to hold the bone fragments in the predetermined position, thus allowing the correct formation between the bone fragments of "bone callus", which gradually restores the lamellar bone tissue with which the bone recovers its original continuity and functionality.

With a hold on the bone far from the centre of fracture and with stabilisation and adjustability outside of the fracture, external fixators allow action on the bone fragments whilst at the same time leaving the fracture zone free for surface medication.

Moreover, external fixators do not interfere with the airing of the fractured part and they prevent the loss of muscle tone normally encountered with the use of plaster casts.

Several years ago, the use of external fixators was extended to a vast range of orthopaedic operations, such as limb lengthening, correction of bone axis rotary and angular deformities, pseudarthrosis, etc. In other words, external fixators are today used as multi-purpose orthopaedic devices, both to correct deformations caused by trauma and to correct pathological deformations.

However, the prior art external fixators are not without disadvantages.

One disadvantage is the fact that in order to implant the bone screws, that is to say, to screw them in, an additional accessory has to be used, in the form of the above-mentioned temporary grip. Obviously, that adds complexity to the operations to be performed, as well as significantly extending the time required, due to the need to connect and then disconnect the temporary grip to and from each screw.

Another disadvantage is limited versatility and discomfort during use.

It should be remembered that the position of the screws is constrained by the presence of muscles, blood vessels, nerves and other soft tissue. When possible, the screws are implanted in such a way that they pass through "safe corridors" in the soft tissue and, therefore, they can emerge from the skin of the patient at various angles and lying in various planes. In practice, it was found that arranging the screws at various angles is more effective for stabilising the fracture.

In prior art external fixators, in particular in those in which the frame has one or more rigid bars which are connected to each other by clamps and joints, the choice of the above-mentioned angles is rather limited, or the desired angles are difficult to achieve with just a few rapid adjustments.

DISCLOSURE OF THE INVENTION

One aim of this invention is to produce an external fixator which is complete in itself, also allowing easy implanting of the screws, that is to say, their screwing in, without the use of additional accessories.

Another aim of this invention is to produce an external fixator which is at the same time effective, versatile and easily and rapidly used.

Accordingly, this invention achieves said aims with a multi-purpose external fixator comprising the features described in one or more of the appended claims.

BRIEF DESCRIPTION OF THE DRAWINGS

The technical features of the invention, with reference to the above aims, are clearly described in the claims below and its advantages are more apparent from the detailed description which follows, with reference to the accompanying drawings which illustrate a preferred embodiment of the invention provided merely by way of example without restricting the scope of the inventive concept, and in which:

FIGS. 2 and 3 are two respective perspective views of a detail of the external fixator of FIG. 1;

FIG. 4 is a view, partly in cross-section, of the detail of FIGS. 2 and 3;

FIG. 5 illustrates an alternative assembly of the detail of FIGS. 2 and 3;

FIGS. 6 and 7 illustrate in cross-section, and in two respective configurations, another detail of the external fixator of FIG. 1; and FIG. 8 is a perspective view of the detail of FIGS. 6 and 7, in the context of FIG. 1.

DETAILED DESCRIPTION OF THE PREFERRED EMBODIMENTS OF THE INVENTION

Figure 1:
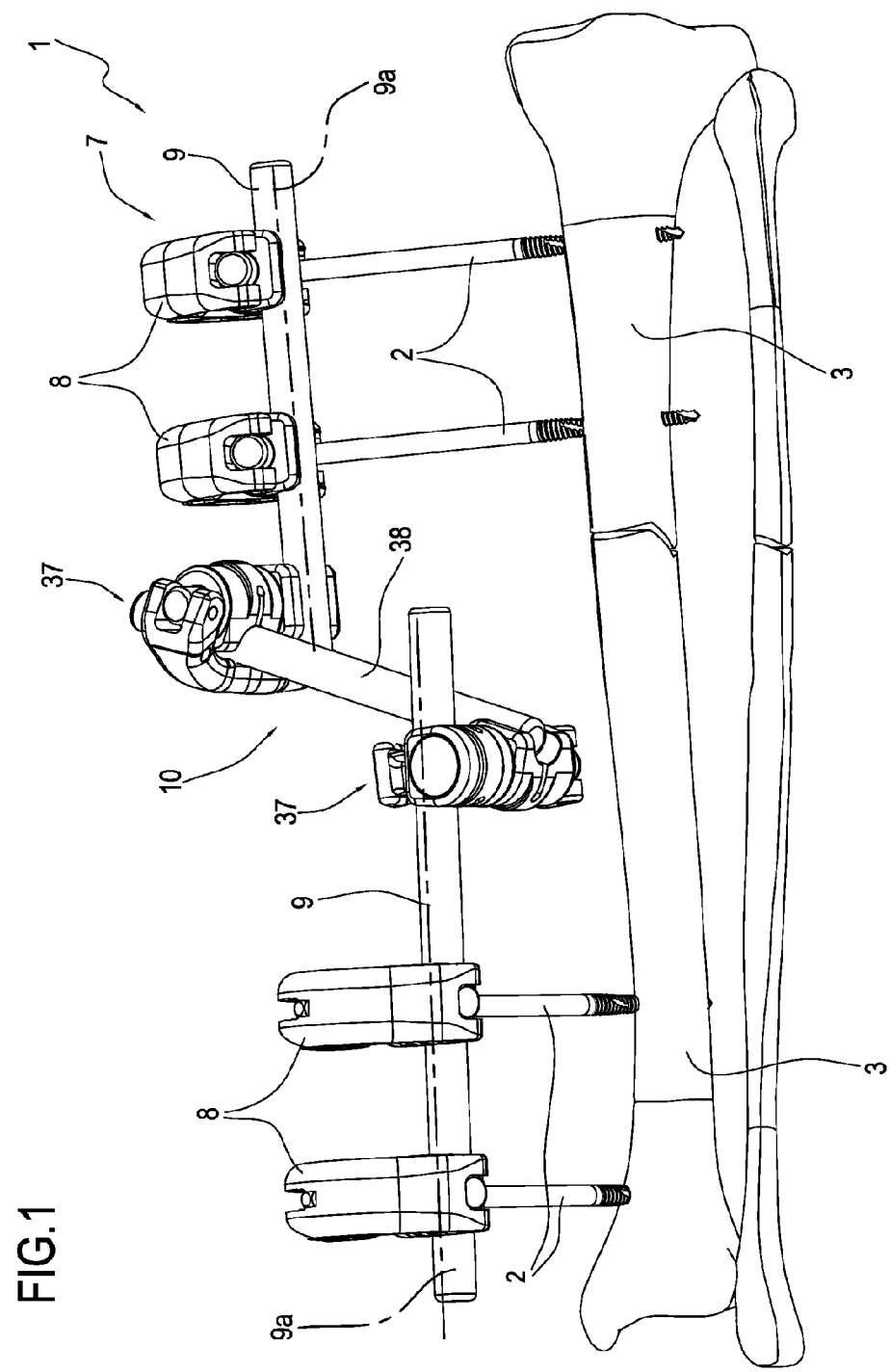
FIG. 1 illustrates an embodiment of the multi-purpose external fixator in accordance with this invention.

In FIG. 1 the numeral 1 denotes in its entirety a multi-purpose external fixator for orthopaedic use.

The fixator 1 may be used both to correct deformations caused by trauma and to correct pathological deformations. For example, the fixator 1 may be used to stabilise a fracture, or in other orthopaedic operations, such as limb lengthening, the correction of bone axis rotary and angular deformities, pseudarthrosis, etc.

The fixator 1 comprises at least one screw 2 to be implanted in a respective bone fragment 3. In particular, for each of the bone fragments 3 extending from the fracture fissure, the fixator 1 comprises at least two screws 2.

As FIG. 4 shows more clearly, each screw 2 comprises a cylindrical body 4, delimited on one side by a threaded end 5 designed to be screwed into the bone fragment 3, and on the other side by a head end 6.

Between the ends 5 and 6, the screw 2 extends along a longitudinal central axis 2a.

The fixator 1 also comprises a rigid external frame 7, for stably anchoring the screws 2.

Once the screws 2 have been implanted in the respective bone fragments 3, the above-mentioned head ends 6, projecting from the skin of the patient together with part of the screw body 4, are anchored to the external frame 7 in order to stably fix the relative position of the screws 2 and, therefore, of the bone fragments 3 around the centre of the fracture.

The external frame 7 comprises a clamp 8 for each screw 2 and at least one bar 9 interconnecting at least two clamps 8.

In particular, the bar 9 has a cylindrical shape.

In the particular example illustrated (FIG. 1), the frame 7 comprises two bars 9, which are each fixed to a pair of clamps 8 and which are stably connected to each other by an articulated connecting unit 10.

The articulated connecting unit 10 also forms part of the frame 7.

As shown in detail in FIG. 4, each clamp 8 comprises a central body 11, with a slot 12 for connection to the screw 2, an element 13 for locking the screw 2 in the slot 12 and a lever 14 for operating the locking element 13.

The central body 11 is substantially cylindrical and extends mainly according to a central longitudinal axis 15.

Along the axis 15, the body 11 is delimited by two longitudinal ends 16, 17, between which a central portion 18 is interposed.

The portion 18 has a reduced diameter and is gradually connected to the ends 16 and 17 by means of respective flared portions 19 whose diameters increase towards the ends 16 and 17.

The above-mentioned slot 12 for the screw 2 is formed by a groove made at the end 17.

The groove extends along a central axis 20 which is at a right angle to the axis 15.

Transversally to the axis 20 the groove has a hook-shaped profile.

Once it is in the slot 12, the axis 2a of the screw 2 coincides with the axis 20 of the slot 12.

The locking element 13 is formed by a tube which can slide along the central body 11.

The locking element 13 is coaxially and rotatably connected to the central body 11 in such a way that it can rotate about the axis 15.

The locking element 13 can be elastically compressed in its direction of sliding along the central body 11, that is to say, in the direction of the axis 15.

In more detail, the element 13 is made of elastically deformable material and comprises a notch 21 transversal to the axis 15, which separates the element 13 into two half-tubes 22 able to slide along the body 11 and spaced in the direction of the axis 15 by a notch 23.

The half-tubes 22 are joined to each other in a U-shape outside the body 11 by a lateral portion 24 of the element 13 extending in the direction of the axis 15.

The above-mentioned U-shaped configuration, together with the elasticity of the material used to make the element 13, allows the elastic compressibility of the element 13 in the direction of the axis 15. However, in alternative embodiments not illustrated, said compressibility may be guaranteed by elastic means interposed between the half-tubes 22, which, in this case, may also be made of rigid and non-deformable material.

A first end 25 of the lever 14 is hinged to the central body 11 on the opposite side of the locking element 13 to the slot 12.

In more detail, the lever 14 is hinged to the above-mentioned end 16 of the body 11 by a pin 26 which is at a right angle to the axis 15. In other words, the half-tubes 22 are interposed between the end 25 of the lever 14 and the slot 12.

The inner cavity which allows the half-tube 22 facing the slot 12 to slide along the central body 11 comprises a reduced section on the side facing the notch 21. Said reduced section forms an end stop 27 which prevents the element 13 from coming off the central body 11 as it slides along the body 11.

At its above-mentioned end 25 the lever 14 comprises a cam 28 for pushing 20 the locking element 13 towards the screw 2 for connection to the slot 12.

The lever 14 can move about the pin 26 from and towards an end position, illustrated in FIGS. 1 to 4, for engagement of the locking element 13 and stable connection of the screw 2 to the slot 12.

In the end position the locking element 13 is compressed between the screw 2, present in the slot 12, and the cam 28, and the half-tubes 22 which are closed to each other.

According to one embodiment of the notch 21, in the above-mentioned end position the half-tubes 22 are at least partly in contact with each other. According to a different embodiment of the notch 21, in the above-mentioned end position the half-tubes 22 are separated from each other but close to one another due to the compression by the lever 14.

The elastic reaction of the element 13 keeps the screw 2 locked in the slot 12, and prevents the screw 2 from sliding axially along the slot 12. That locking is guaranteed by the force of friction between the screw 2 and the half-tube 22 in contact with it, on one side, and between the screw 2 and the slot 12, on the other.

The elastic reaction of the element 13, keeping the screw 2 locked in the slot 12 also prevents it from rotating relative to the clamp 8, about the axis 2a, thus forming a torsional constraint.

The screw 2 is also prevented from coming out of the slot 12 in a direction 10 transversal to the axis 20 by the above-mentioned hook-shaped profile of the slot 12.

In the end position the lever 14 and the screw 2 are positioned in a T-shaped configuration relative to each other, in which the clamp 8, and more precisely the lever 14, forms a grip for implanting the screw 2 in the bone fragment 3. For that purpose, between its end 25 hinged to the central body 11 and its free end 29, which is opposite the end 25, the lever 14 comprises a curved connecting stretch 30.

In other words, the lever 14 has the shape of an arc.

The stretch 30 is anatomically shaped to allow the clamp 8 to be comfortably gripped when used as an accessory for screwing in the screws.

In the end position, in particular during use of the clamp 8 as an accessory for screwing in the screws, the connecting stretch 30 preferably has its concavity facing in the direction of longitudinal extension of the screw 2, that is to say, in the direction of the axis 2a, towards the threaded end 5 of the screw.

More generally, in the end position the connecting stretch 30 preferably has its concavity facing in the direction of the axis 20 of the slot 12, towards the slot 12.

As FIGS. 2 and 3 show more clearly, the lever 14 comprises two prongs 31, formed by two separated ribs of the stretch 30 and two respective separate portions of the end 29.

With the exception of an initial stretch 32 whose prongs branch off, the distance between the prongs 31 is at least equal to the diameter of the cylindrical body 4 of the screw 2 to prevent any interference between the lever 14 and the screw 2 in the movement of the lever 14 from and towards the above-mentioned end position. If necessary, this also allows alternative assembly of the clamp 8 on the screw 2, inverted relative to that described above. That is to say, with the lever 14 in the end position the stretch 30 of the lever has its convex side facing in the direction of the axis 2a towards the threaded end 5 of the screw 2 (FIG. 5).

Said alternative assembly is preferably only limited to use of the clamp 8 as an element of the frame 7. The possibility of assembling the frame 7 according to the two different embodiments described above gives the fixator 1 obvious versatility.

At the stretch 32, the distance between the prongs 31 is just greater than the transversal dimension of each of the four faces 33 forming the lateral perimeter of the head end piece 34 of the screw 2. This forms a shape impediment to relative rotation of the clamp 8 and the screw 2 during use of the clamp 8 as an accessory for screwing in the screw.

Between the ends 25 and 29 the fixator 1 comprises two stiffening sides 57, which extend at a right angle from the stretch 30 and comprise one or more lightening openings.

The clamp 8 comprises a slot 35 for connection to the bar 9. In particular, the slot 35 is made in the locking element 13 and is formed by a groove made between the half-tubes 22 on the side diametrically opposed to the above-mentioned lateral portion 24 of the element 13.

In particular, the groove has a semi-cylindrical profile whose diameter is just greater than the diameter of the bar 9.

The groove extends along a central axis 36 which is at a right angle to the axis 15.

Once it is in the slot 35, the longitudinal axis 9a of the bar 9 coincides with the axis 36 of the slot 35.

The slot 35 is located at the central portion 18 of the body 11 which has a reduced diameter.

The reduction in the diameter of the portion 18 and the fact that the slot 35 is at the portion 18 allow the bar 9 to be fitted as close as possible to the axis 15, thus guaranteeing advantageous compactness in the assembly, in particular in the alternative assembly shown in FIG. 5.

It is important to highlight that, with the lever 14 in the above-mentioned end position, the locking element 13 stably and simultaneously connects the screw 2 to the respective slot 12 of the central body 11, on one side, and the bar 9 to the respective slot 35, on the other. In particular, with the lever 14 in the above-mentioned end position, the cam 28 compresses and locks the locking element 13 relative to the central body 11 in a position in which the locking element 13 stably and simultaneously connects the screw 2 to the respective slot 12 of the central body 11, on one side, and the bar 9 to the respective slot 35 of the locking element 13, on the other.

Locking of the bar 9 in the slot 35 is guaranteed by the force of friction produced between the bar 9 and the locking element 13.

It is important to emphasise that simultaneous locking of the screw 2 and the bar 9 in the clamp 8 allows easy selection and holding of the position of the bar 9 relative to the axis 2a of the screw 2. It is possible to rotate, even simultaneously, the entire clamp 8 and therefore the bar 9 about the axis 2a, and the locking element 13, and therefore the bar 9, about the axis 15.

In other words, to select the position of the bar 9 relative to the axis 2a of the screw 2 it is possible to rotate, even simultaneously, the bar 9 about the axis 2a of the screw 2 and about an axis (the axis 15) which is at a right angle to the axis 2a, before fixing the position with a single movement consisting of rotation of the lever 14 towards its end position, described above.

In the particular example illustrated (FIG. 1), the articulated connecting unit 10 comprises two joint elements 37 and a connecting bar 38.

The bar 38 is like the above-mentioned bars 9. In particular, the bar 38 is identical to and interchangeable with the bars 9.

Obviously, the bars 9 and 38 may be part of a kit consisting of bars of various lengths and the same diameter.

As can be seen more clearly in FIGS. 6, 7 and 8, each joint element 37 comprises a central body 39, a pair of locking elements 40, like the locking element 13 described above, and a lever 41 for operating the locking elements 40. Each locking element 40 is designed to receive and lock a respective bar 9 or 38 in the joint element 37.

The central body 39 is substantially cylindrical and extends mainly according to a central longitudinal axis 42.

Along the axis 42, the body 39 is delimited by two longitudinal ends 43, 44, between which a central portion 45 is interposed.

The central portion 45 comprises an intermediate stretch 46 with a diameter equal to that of the ends 43 and 44. Between the intermediate stretch 46 and each of the ends 43 and 44, the body 39 comprises a stretch 47 with reduced diameter. Each stretch 47 is gradually connected to the intermediate stretch 46 and to the respective end 43, 44 by flared portions, like the portions 19 described above.

Each locking element 40 is formed by a tube which can slide along the central body 39.

The locking elements 40 are coaxially and rotatable connected to the central body 39 in such a way that they can rotate independently about the axis 42.

The locking elements 40 can be elastically compressed in their direction of sliding along the central body 39, that is to say, in the direction of the axis 42.

In more detail, each element 40 is made of elastically deformable material and comprises a notch 48 transversal to the axis 42, which separates the element 40 into two half-tubes 49 able to slide along the body 39 and spaced in the direction of the axis 42 by a notch 50.

The half-tubes 49 are joined to each other in a U-shape outside the body 39 by a lateral portion 51 of the element 40 extending in the direction of the axis 42.

The above-mentioned U-shaped configuration, together with the elasticity of the material used to make the element 40, allows the elastic compressibility of the element 40 in the direction of the axis 39. However, in alternative embodiments not illustrated, said compressibility may be guaranteed by elastic means interposed between the half-tubes 49, which, in this case, may also be made of rigid and non-deformable material.

Each locking element 40 comprises a slot 55 for connection to the bar 9 or to the bar 38.

In particular, the slot 55 is a semi-cylindrical groove made between the half-tubes 49 on the side diametrically opposed to the above-mentioned lateral portion 51 of the element 40. The groove extends along a central axis 56 which is at a right angle to the axis 42.

Advantageously, but not necessarily, the slot 55 surface is textured and/or material is added, in such a way as to give the surface a high coefficient of friction. Once it is in the slot 55, the longitudinal central axis 9a or 38a of the bar 9 or 38 coincides with the axis 56 of the slot 55.

Each slot 55 is located at a respective stretch 47 of the body 39 which has a reduced diameter.

The reduction in the diameter of the stretches 47 and the fact that the slots 55 are at the stretches 47 allow the bars 9 and 38 to be fitted as dose as possible to the axis 42, thus guaranteeing advantageous compactness in the assembly of the articulated connecting unit 10.

The lever 41 Is hinged to the end 43 of the body 39 by a pin 52 which is at a right angle to the axis 42.

The end 44 of the body 39 supports an end stop 53 which prevents the locking elements 40 from coming off the central body 39 as they slide along the body 39.

At its above-mentioned end hinged to the body 39 the lever 41 comprises a cam 54 for pushing the locking elements 40 towards the end stop 53.

The lever 41 can move about the pin 52 away from and towards an end position, illustrated in FIGS. 6 and 8, for engagement of the locking elements 40. In the end position, the locking elements 40 are compressed between the end stop 53 and the cam 54, as well as around the bars 9 and 38.

The elastic reaction of the elements 40 keeps the bars 9 and 38 locked in the respective slots 55. Said locking is guaranteed by the force of friction between the bars 9 and 38 and the respective slots 55.

Advantageously, according to alternative embodiments not illustrated, means are provided for preventing relative rotation of the adjacent elements 40, such as washers made of a material with a high coefficient of friction or even surface finishes or texture able to obstruct said rotation.

It is important to highlight that, with the lever 41 in the above-mentioned end position, the locking elements 40 stably and simultaneously connect the bars 9 and 38 to the joint element 37.

It is also important to point out that the simultaneous locking of the bars 9 and 38 in the joint element 37, together with the versatility of assembly offered by the clamps 8, allows the frame 7 assembly configuration to be easily selected and maintained.

It is possible to rotate, even simultaneously, the two elements 40 about the axis 42, and therefore reciprocally the bar 9 and 38, before locking their position relative to each other with a single movement consisting of rotation of the lever 41 towards its end position, described above.

From the above description, it is evident that, according to an alternative embodiment of the configuration shown in FIG. 1, the two bars 9 may be connected to each other directly by a joint element 37.

In another alternative embodiment, not illustrated, the fixator 1 comprises an articulated connecting unit 10 comprising more than one bar 38 and more than two joint elements 37.

In another alternative embodiment, not illustrated, the fixator 1 comprises a single bar 9 for interconnecting the clamps 8, and the articulated connecting unit 10 is absent.

The fixator 1 described above is made of materials which render it radiolucent, as well as compatible with magnetic resonance imaging. In particular, the bar 9 (or each bar 9 if the frame 7 comprises more than one bar 9), the locking element 13 and the lever 14 are made of composite material, in particular epoxy, filled with carbon powder. The central body 11 is made of aluminum. Each screw 2 is made of titanium.

Similarly, the bar 38 (or each bar 38 if the frame 7 comprises more than one bar 38), the locking elements 40 and the lever 41 are made of composite material, in particular epoxy, filled with carbon powder. The central body 39 is made of aluminium.

The invention described above achieves the preset aims. The fixator 1 is complete in itself, allowing, by means of its clamps 8, even easy implanting of the screws 2, without having to use additional accessories.

Moreover, the fixator 1 is at the same time effective, versatile and easily and rapidly used. This is guaranteed by the fact that the fixator 1 requires just a few rapid adjustments. In particular, simple rotations of the levers 14 and 41 allow simultaneous locking of the relative positions of two or more components of the fixator 1.

Obviously, the invention preferably comprises safety fastening means for the levers 14 and 41 to prevent them from accidentally rotating towards their respective release positions. The safety fastening means may be, for example, safety pegs.

It is also evident that, to facilitate use of the fixator in emergency conditions, in the kit supplied to first response medical personnel the clamps may be ready-assembled on the screws, ready to screw them in.

The invention described above is susceptible of industrial application and may be modified and adapted in several ways without thereby departing from the scope of the inventive concept. Moreover, all details of the invention may be substituted by technically equivalent elements.

The invention claimed is:

1. A multi-purpose external fixator, comprising:
at least one screw for implantation in a bone fragment; and
a frame having at least one damp and at least one interconnecting bar;
the damp comprising:
a central body, having a first slot for receiving the screw;
a locking element for locking the screw in the first slot, the central body being movably connected to the locking element such that the screw positioned in the first slot is movable between a position of locking engagement with the locking element and a position of locking disengagement with the locking element, at least one chosen from the locking element and the central body comprising a second slot for receiving the at least one interconnecting bar; and
a lever for operating the locking element; the lever having a hinge portion being hinged to one chosen from the central body and the looking element, the lever including a cam for engaging an other of the central body and the locking element, the lever movable from and towards a locked position whereby the central body is caused to move with respect to the locking element by the action of the cam on the other of the central body and the locking element to create a force path between the cam and the hinge portion that transfers force between the central body and the locking element via engagement of the screw between the central body and the locking element to lock the screw to the first slot independently of whether the at least one interconnecting bar is positioned in the second slot; in the locked position, the lever and the screw being positioned in a configuration relative to each other, in which the lever forms a grip for implanting the screw in the bone fragment;

wherein when the at least one interconnecting bar is positioned in the second slot, the force path between the cam and the hinge portion that locks the screw to the first slot also causes the second slot to lock the at least one interconnecting bar simultaneously with locking the screw to the first slot, the lever acting on the at least one interconnecting bar substantively enough to lock the at least one interconnecting bar only via the force path between the cam and the hinge portion;

wherein the lever comprises a first end which is hinged to the central body, a second, free end, opposite the first end, and a screw locking portion positioned between the first and second free ends, the screw locking portion including a shape impediment for engaging a counterpart locking portion of the screw to prevent relative rotation between the lever and the screw, the shape impediment at least partially surrounding and engaging the counterpart locking portion of the screw as the lever is moved to the locked position and disengaging the counterpart locking portion of the screw as the lever is moved to an unlocked position where the lever is positioned free of the screw and the screw is in the position of locking disengagement with the locking element.

2. The external fixator according to claim 1, wherein the lever comprises a curved connecting stretch between the first and second ends.

3. The external fixator according to claim 2, wherein in the locked position, a concave portion of the connecting stretch faces in a direction of longitudinal extension of the screw towards a threaded end of the screw.

4. The external fixator according to claim 1, wherein the lever is hinged to the central body on an opposite side of the locking element to the first slot.

5. The external fixator according to claim 4, wherein the locking element comprises a tube which is slideable along the central body.

6. The external fixator according to claim 5, wherein the locking element is elastically compressible in a direction of sliding along the central body.

7. The external fixator according to claim 5, wherein the locking element is made of elastically deformable material.

8. The external fixator according to claim 5, wherein, in the locked position, the cam compresses the locking element and locks the locking element relative to the central body in a position in which the locking element stably and simultaneously connects the screw to the first slot in the central body, on one side, and the at least one interconnecting bar to the second slot in the locking element, on another side.

9. The external fixator according to claim 8, wherein the cam has an over center engagement with the locking element about the hinged connection such that an elastic reaction force of the locking element against the cam provides a biasing force on the lever in a direction of locking when the lever is in the locked position, the biasing force thereby maintaining the lever in the locked position.

10. The external fixator according to claim 1, wherein the central body has a substantially cylindrical shape and the locking element is coaxially and rotatably connected to the central body to rotate about a longitudinal axis of the central body.

11. The external fixator according to claim 10, wherein the frame comprises the at least one interconnecting bar between at least two clamps; the second slot having a longitudinal axis oriented at a right angle to the longitudinal axis of the central body.

12. The external fixator according to claim 1, wherein the frame comprises the at least one interconnecting bar between at least two clamps and each clamp comprises a second slot for connection to the at least one interconnecting bar; wherein, with the lever in the locked position, the locking element stably and simultaneously connects the screw to the first slot in the central body, on one side, and the at least one interconnecting bar to the second slot, on the other.

13. The external fixator according to claim 12, wherein the second slot for connection to the bar is positioned in the locking element.

14. The external fixator according to claim 13, wherein the central body has a substantially cylindrical shape and the locking element is coaxially and rotatably connected to the central body to rotate about a longitudinal axis of the central body.

15. The external fixator according to claim 14, wherein the second slot for connection to the at least one interconnecting bar has a longitudinal axis oriented at a right angle to the longitudinal axis of the central body.

16. The external fixator according to claim 1, wherein the counterpart locking portion of the screw comprises a plurality of locking faces positioned around a circumference of the screw and a plurality of corner portions positioned respectively between the plurality of locking faces, each of the plurality of locking faces positioned at a same axial position on the screw with a first width across flats dimension formed between two of the locking faces parallel and facing away from one another and a width across corners dimension formed between opposite corner portions adjacent the parallel locking faces, the shape impediment including a slot portion positioned on the lever, the slot portion having two slot faces facing one another with a second width across flats dimension formed between the two slot faces, the second width across flats dimension sized larger than the first width across flats dimension to permit movement and alignment of the two slot faces with respect to the two locking faces when the lever is moved from the unlocked position to the locked position;

the second width across flats dimension sized smaller than the width across corners dimension such that when the lever is in the locked position and the two slot faces are positioned axially adjacent the two locking faces, at least one of the two slot faces will block at least one of the corner portions and prevent rotation of the clamp relative to the screw.

17. The external fixator according to claim 1, wherein the counterpart locking portion of the screw comprises a plurality of locking faces positioned around a circumference of the screw and a plurality of corner portions positioned respectively between the plurality of locking faces, each of the plurality of locking faces positioned at a same axial position on the screw, the screw having a minor diameter at the locking faces representing a minimum distance across the screw at the locking faces and a major diameter at the locking faces at a same axial position as the minor diameter and representing a maximum distance across the screw at the corner portions the shape impediment including a slot portion positioned on the lever, the slot portion having two slot faces facing one another with a minor width dimension formed between the two slot faces representing a minimum distance across the slot faces at a portion of the slot portion positioned adjacent the screw when in the locked position, the minor width dimension sized larger than the minor diameter to permit movement and alignment of the two slot faces with respect to the two locking faces when the lever is moved from the unlocked position to the locked position;

the minor width dimension sized smaller than the major diameter such that when the lever is in the locked position and the two slot faces are positioned axially adjacent the two locking faces, at least one of the two slot faces will block at least one of the corner portions and prevent rotation of the clamp relative to the screw.

18. A multi-purpose external fixator, comprising:
at least one screw for implantation in a bone fragment; and
a frame having at least one clamp;
the clamp comprising:
- a central body, having a first slot for connection to the screw;
- a locking element for locking the screw n the first slot; and
- a lever for operating the locking element; the lever being hinged to the central body and movable from and towards a locked position for engagement of the locking element and stable connection of the screw to the first slot; in the locked position, the lever and the screw being positioned in a configuration relative to each other, in which the lever forms a grip for implanting the screw in the bone fragment;
- wherein the lever comprises a cam for pushing the locking element towards the slot for connection to the screw,
- wherein the cam has an over center engagement with the locking element about the hinged connection such that an elastic reaction force of the locking element against the cam provides a biasing force on the lever in a direction of locking when the lever is in the locked position, the biasing force thereby maintaining the lever in the locked position;
- wherein the lever comprises a first end which is hinged to the central body, a second, free end, opposite the first end, and a screw locking portion positioned between the first and second free ends, the screw locking portion including a shape impediment for engaging a counterpart locking portion of the screw to prevent relative rotation between the lever and the screw, the shape impediment at least partially surrounding and engaging the counterpart locking portion of the screw as the lever is moved to the locked position and disengaging the counterpart locking portion of the screw as the lever is moved to an unlocked position where the lever is position free of the screw and the screw is unlocked from the locking element.

19. A multi-purpose external fixator, comprising:
at least one screw for implantation in a bone fragment; and
frame having at least one clamp;
the clamp comprising:
- a central body, having a first slot for connection to the screw;
- a locking element for locking the screw in the first slot; and
- a lever for operating the locking element; the lever being hinged to the central body and movable from and towards a locked position for engagement of the locking element and stable connection of the screw to the first slot; in the locked position, the lever and the screw being positioned in a configuration relative to each other, in which the lever forms a grip for implanting the screw in the bone fragment;
wherein the lever comprises a first end which is hinged to the central body, a second, free end, opposite the first end, and a screw locking portion positioned between the first and second free ends, the screw locking portion including a shape impediment for engaging a counterpart locking portion of the screw to prevent relative rotation between the lever and the screw, the shape impediment at least partially surrounding and engaging the counterpart locking portion of the screw as the lever moved to the locked position and disengaging the counterpart locking portion of the screw as the lever is moved to an unlocked position where the lever is positioned free of the screw and the screw is unlocked from the locking element, wherein the counterpart locking portion of the screw comprises a plurality of locking faces positioned around a circumference of the screw and a plurality of corner portions positioned respectively between the plurality of locking faces, each of the plurality of locking faces positioned at a same axial position on the screw, the screw having a minor diameter at the locking faces representing a minimum distance across the screw at the locking faces and a major diameter at the locking faces at a same axial position as the minor diameter and representing a maximum distance across the screw at the corner portions, the portion forming the shape impediment including a slot portion positioned on the lever, the slot portion having two slot faces facing one another with a minor width dimension formed between the two slot faces representing a minimum distance across the slot faces at a portion of the slot portion positioned adjacent the screw when in the locked position,
the minor width dimension sized larger than the minor diameter to permit movement and alignment of the two slot faces with respect to the two locking faces when the lever is moved from the unlocked position to the locked position;
the minor width dimension sized smaller than the major diameter such that when the lever is in the locked position and the two slot faces are positioned axially adjacent the two locking faces, at least one of the two slot faces will block at least one of the corner portions and prevent rotation of the clamp relative to the screw.

* * * * *